US009060924B2

(12) United States Patent
Tawashi et al.

(10) Patent No.: US 9,060,924 B2
(45) Date of Patent: Jun. 23, 2015

(54) TOPICAL FORMULATIONS CONTAINING PALM POLLEN

(75) Inventors: Rashad Tawashi, Beaconsfield (CA); Mona Tawashi, Los Altos, CA (US)

(73) Assignee: ClinAvenir, LLC, Los Altos, CA (US)

( * ) Notice: Subject to any disclaimer, the term of this patent is extended or adjusted under 35 U.S.C. 154(b) by 207 days.

(21) Appl. No.: 13/539,855

(22) Filed: Jul. 2, 2012

(65) Prior Publication Data

US 2013/0011349 A1    Jan. 10, 2013

Related U.S. Application Data

(60) Provisional application No. 61/505,900, filed on Jul. 8, 2011.

(51) Int. Cl.
| | |
|---|---|
| *A61K 36/889* | (2006.01) |
| *A61K 9/00* | (2006.01) |
| *A61Q 19/08* | (2006.01) |
| *A61Q 19/00* | (2006.01) |
| *A61K 8/97* | (2006.01) |
| *A61Q 1/06* | (2006.01) |
| *A61Q 17/04* | (2006.01) |
| *A61Q 19/10* | (2006.01) |

(52) U.S. Cl.
CPC .............. *A61K 9/0014* (2013.01); *A61K 36/889* (2013.01); *A61Q 1/06* (2013.01); *A61Q 17/04* (2013.01); *A61Q 19/08* (2013.01); *A61Q 19/10* (2013.01); *A61Q 19/00* (2013.01); *A61K 8/975* (2013.01)

(58) Field of Classification Search
USPC .................................................. 424/727, 725
IPC ..................................................... A61K 36/889
See application file for complete search history.

(56) References Cited

U.S. PATENT DOCUMENTS

| | | | | |
|---|---|---|---|---|
| 4,528,267 | A * | 7/1985 | Calenoff et al. | 435/7.92 |
| 4,716,120 | A * | 12/1987 | Tsay et al. | 424/276.1 |
| 4,751,791 | A * | 6/1988 | Al-Rawi | 47/1.41 |
| 5,013,552 | A | 5/1991 | Amer et al. | |
| 5,275,819 | A | 1/1994 | Amer et al. | |
| 6,790,464 | B2 * | 9/2004 | Kuok et al. | 424/725 |
| 7,883,726 | B2 | 2/2011 | Crutchfield, III | |
| 2002/0121046 | A1 * | 9/2002 | Yamashita | 47/58.1 SC |
| 2005/0048020 | A1 | 3/2005 | Willie | |
| 2005/0063994 | A1 * | 3/2005 | Caplan et al. | 424/200.1 |
| 2009/0214628 | A1 | 8/2009 | De Rijk | |
| 2010/0138951 | A1 * | 6/2010 | Nelson et al. | 800/268 |

FOREIGN PATENT DOCUMENTS

| | | |
|---|---|---|
| WO | WO 92/19229 | 11/1992 |
| WO | WO 98/50005 A1 | 11/1998 |

OTHER PUBLICATIONS

Alqarni, A. J. Biol. Sci. 2006, vol. 6, No. 4, pp. 734-737.*
Hassan, Hazem M.M., Chemical Composition and Nutritional Value of Palm Pollen Grains, 2011, Global J. Biotech & Biochem, 6(1): 01-07.
Bahmanpour S., et. al., Effect of Poenix Dactylifera Pollen on Sperm Parameters and Reproductive System of Adult Male Rats, Iran J. Med Sci., Dec. 2006; vol. 31, No. 4: 208-212.
Bennett, R.D., et al, Isolation of Estrone and Cholesterol from the Date Palm, *Phoenix Dactylifera* L. Phytochemistry, Mar. 1966; 5(2): 231-235.
El-Ridi, M.S., et al.,Gonadotrophic Hormones in Pollen Grains of the Date Palm, Z Naturforsch B., Jan. 1960; 15B: 45-9.
El-Ridi, M.S., et al., Isolation of Rutin from the Pollen Grain of the Date Palm, (Dactylifera Palma L.), Arch Biochem Biophys., Aug. 1952; 39(2): 317-21.
Hassan, A., et al., An Oestrogenic Substance in Pollen-Grains of Date Palm Tree *Phoenix dactylifera* L., Palmae, Nature, Mar. 22, 1947; 159(4038):409.
Hess, R.A., Estrogen in the Adult Male Rat Reproductive Tract: A Review, Reprod Biol Endocrinol, Jul. 9, 2003; 1: 52.
Mahran, G.H., et al., A Phytochemical Study of Date Palm Pollen, Planta Med., 1976; 29(2): 171-175.
Soliman, F.A., et al., The Gonadotrophic Activity of Date Palm Pollen Grains, Experientia, Oct. 15, 1957;13(10):411-2.
Schroeder, P., et al., Photoprotection Beyond Ultraviolet Radiation—Effective Sun Protection has to Include Protection Against Infrared A Radiation-induced Skin Damage, Skin Pharmacol Physiol, 2010;23(1): 15-7.
Thiele, J., et. al., Oxidants and Antioxidants in Cutaneous Biology, Current Problems in Dermatology, 1996; vol. 29; 137.
Werner, N., et al., Sex Hormones Save our Skin: The Vascular Networking of Estrogen, Circulation Research, 2009; 104: 135.
PCT/US2012/043653, Aug. 22, 2012, International Search Report (1 pg.).
Abbas et al., "Estradiol, Esteriol, Estone and Novel Favonoids from Date Palm Pollen," Australian Journal of Basic and Applied Sciences (2011) 5(8):606-614.
Naidu et al., "Chemotherapy-Induced and/or Radiation Therapy-Induced Oral Mucositis—Complicating the Treatment of Cancer," Neoplasia (2004) 6(5): 423-431.
Ziya Al-Din Abdullah Ibn Al-Baitar Al-Jaam'e-li-Mufradaat-al-Advia-Aghzia vol. I (13th century AD) pp. 5 (page No. 05-09) ( Ref:pg. no.of publication:112 ) Publication Date—1874 AD Matba Amra Cairo Place of Publication Egypt, India.†
Mohammad Azam Khan Muheet Azam vol. II ( Part II) (19th century AD) pp. 4 (page No. 10-13) (Ref.pg. no.of publication:26) Publication Date—1898 AD Matba Nizami Place of Publication—Kanpur, India.†
Ziya Al-Din Abdullah Ibn Al-Baitar Al-Jaam'e-Il-Mufradaat-al-Advia-wal-Aghzia vol. 11 (13th century AD) pp. 6 (page No. 14-19) (Ref.pg. no.of publication: 105) Publication Date—1874 AD Matba Amra Cairo Place of Publication—Egypt. India.†
Madhavah Ayurvedaprakasah pp. 5 (page No. 20-24) (Ref.pg. no.of publication:265) Publication Date—Edn. Reprint 1999 Chaukhamba Bharati Academy Place of Publication—Varanasi. India.†

(Continued)

*Primary Examiner* — Chris R Tate
(74) *Attorney, Agent, or Firm* — Jill A. Jacobson

(57) ABSTRACT

Compositions are provided that include date palm pollen or an extract thereof. The compositions may be formulated for topical use in methods of treatment or prophylaxis of various skin conditions or methods to counteract the effects of skin aging.

17 Claims, No Drawings

(56) References Cited

OTHER PUBLICATIONS

Vagabhata Astanga Hrdaya pp. 5 (page No. 25-29) (Ref.pg. no.of publication:890) Publication Date—edn. 8th 1998 Chaukhamba Orientalia Place of Publication—Varanasi, India.†

Bogar Boga Munivar Vaithyam-700 pp. 4 (page No. 30-33) (Ref.pg. no.of publication:36) B.Rathina Nayakar Sons Place of Publication—Chennal. India.†

Bharata Bhaisajya Ratnakara vol.-V pp. 8 (page No. 34-41) (Ref. pg. no.of publication:249-250 ) Publication Date—Edn. 2nd. Reprint, Aug. 1999 B. Jain Publishers Place of Publication—New Delhi, India.†

Nighanturatnakarah pp. 7 (page No. 42-48) (Ref:pg. no.of publication:141) Publication Date—Edn. 1867 Vishnu Vasudev Godbole Place of Publication—Bombay, India.†

Manthana Bhairava Anandakandah pp. 7 (page No. 49-55) (Ref.pg. no.of publication:268) Publication Date—Edn. 1st 1952 T.M.S.S.M. Library Place of Publication—Madras,. India.†

\* cited by examiner

† cited by third party

TOPICAL FORMULATIONS CONTAINING PALM POLLEN

CROSS-REFERENCE TO RELATED APPLICATIONS

This application claims the benefit of U.S. Provisional Application No. 61/505,900, filed on Jul. 8, 2011, which is incorporated by reference herein in its entirety.

FIELD OF THE INVENTION

The invention relates to use of palm pollen for treatment of skin conditions and anti-aging treatment.

BACKGROUND

The last decade has seen a plethora of new research on anti-aging systems. There have been dramatic improvements in laser technology, injectable fillers, and various advanced formulations intended for photo-protection, moisturizing or tissue repair. The treatments available today typically require the application of more than one treatment strategy. In most cases, the treatment is complicated by the need for a multiple step solution and long waiting periods to observe tangible results.

Botox® is a popular strategy known for its anti-aging benefits. However, Botox® is a costly treatment that requires physician administered injections and targets specific muscles. Although Botox® reduces the appearance of wrinkles, it requires repeated treatments and is often associated with an artificial plastic appearance.

There is a need for an alternative solution that takes into consideration the extrinsic and intrinsic factors that affect skin aging and that integrates benefits of current anti-aging systems by providing a simple, natural means of returning skin to a more youthful appearance.

BRIEF SUMMARY OF THE INVENTION

Compositions, methods, and kits are provided for prophylaxis, treatment, or cure of skin conditions. The compositions described herein include date palm pollen (DPP) or an extract thereof. Methods of use that include topical administration of a DPP-containing composition to an individual are also provided.

In one aspect, a composition is provided that contains pollen from a palm species of the genus *Phoenix*, or an extract thereof, and is formulated for topical application, e.g., to an external body surface of an individual, such as the skin. A composition as described herein (e.g., a composition described as containing or including "DPP or an extract thereof") may contain DPP, an extract of DPP, or both DPP and an extract of DPP. In some embodiments, the composition described as containing "DPP or an extract thereof" contains DPP and does not contain an extract of DPP. In some embodiments, the composition described as containing "DPP or an extract thereof" contains an extract of DPP and does not contain DPP. In some embodiments, the composition may contain both DPP and an extract of DPP. In one embodiment, the composition contains date DPP or an extract thereof from *Phoenix dactylifera* L. In various embodiments, the composition may be formulated as a powder, a compact disc, a suspension, a cream, a lotion, an ointment, a gel, a foam, a paste, an aerosol, a body wash, a hair product, a sunscreen, a lipstick, an emulsion, a spray, a cosmetic, or an anhydrous absorption base composition. In some embodiments, the composition also contains a fragrance. The composition may be formulated in some embodiments for application to facial skin.

The composition may contain at least one additional constituent to facilitate topical application. For example, the composition may contain one or more flow regulating agent(s) such as, for example, colloidal silica, magnesium trisilicate, and/or cornstarch. In some embodiments, a composition that contains a flow regulating agent is formulated as a powder or compact disc composition. In some embodiments, the composition is formulated as a compact disc and contains one or more flow regulating agent(s), one or more filler(s) (for example, titanium dioxide, spray dried lactose, and/or starch), and optionally one or more excipient(s) (for example, magnesium stearate). The excipient(s) may be included to facilitate compression.

In some embodiments, the composition is formulated as a suspension and contains one or more alcohol(s) (for example, isopropyl alcohol and/or ethyl alcohol), optionally one or more preservative(s) (for example, benzalkonium chloride, benzyl alcohol, and/or one or more paraben(s)), and optionally one or more suspending agent(s) (for example, carboxymethyl cellulose and/or xanthan gum). In one embodiment, the suspension formulation is a photoprotective formulation, such as a sunscsreen formulation.

In some embodiments, the composition is formulated as a cream and contains one or more surfactant(s) (for example, sorbitan monostearate, and/or polysorbate (e.g., polysorbate 60, polysorbate 20)), one or more preservative(s) (for example, methylparaben, proplyparaben, and/or benzyl alcohol), and one or more stabilizer(s) (for example, sorbitol, glycerine, and/or glyceryl laurate), an oil phase (for example, stearic acid, cetyl alcohol, and/or isopropyl palmitate), and an aqueous phase. Surfactant(s), preservative(s), stabilizer(s), and/or DPP or DPP extract may partition to the aqueous phase (water) in a cream formulation as described herein. In one embodiment, surfactant(s), preservative(s), stabilizer(s), and DPP or DPP extract all partition to the aqueous phase. In one embodiment, the cream formulation is a vanishing cream. In one embodiment, the cream formulation is a photoprotective formulation, such as a sunscreen formulation.

In some embodiments, the composition is formulated for treatment of a skin condition. For example, the composition may be formulated for treatment of psoriasis, acne, atopic dermatitis, actinic keratosis, scleroderma, rosacea, eczema, an allergic skin disorder, radiation and/or chemotherapy induced mucositis, or a combination thereof. In certain embodiments, the composition may contain one more additional compound(s) for treatment of the skin condition, for example, one or more a pharmaceutical compound(s) for treatment of at least one symptom of the skin condition.

In some embodiments, the composition is formulated for prophylaxis or prevention of occurrence of a skin condition and/or for lessening the severity of a skin condition if it should occur. In one embodiment, the skin condition is skin cancer.

In some embodiments, the composition is formulated to ameliorate or lessen the visual appearance of at least one effect of aging, for example, wrinkles, lines, skin dryness, dark spots, reduction in skin elasticity, increase in skin roughness, or a combination thereof. In some embodiments, the composition is formulated for application to facial skin or another external body surface in an anti-aging treatment.

In some embodiments, the composition is formulated for application to facial skin or another external body surface to reduce oil (e.g., facial oil), enlarged pores, blackheads, or a combination thereof.

In some embodiments, the composition is formulated for protection of skin from environmental damage, radiation therapy, chemotherapy, or photoaging. In certain embodiments, the environmental damage includes skin damage due to exposure to ultraviolet radiation (for example, UVA and/or UVB radiation), infrared radiation, or a combination thereof. The composition for protection of skin from environmental damage or photoaging may be formulated as a photoprotective formulation, for example, a sunscreen.

In another aspect, a composition is provided for delivery of one or more compound(s) to an external body surface, such as the skin. The composition contains DPP or an extract thereof. A composition formulated for delivery of a compound to the skin may comprise pollen from a palm species of the genus *Phoenix*, or an extract thereof, for example, DPP or an extract thereof from *Phoenix dactylifera* L. In certain embodiments, the composition may be formulated for delivery of a steroidal compound, a plant steroidal compound, a glycoside compound, a gonadotrophic hormone, a carotenoid, a glucoprotein, a bioflavinoid, a triterpinoid, and/or an antioxidant. In some embodiments, the compound(s) to be delivered is (are) contained within or derived from the DPP or extract thereof. In some embodiments, the composition may be formulated for delivery of an estrogenic hormone, such as estrone, a bioflavinoid, such as rutin, and/or a triterpinoid, such as β-amyrin.

In another aspect, kits are provided that contain any of the DPP and/or DPP extract containing compositions described herein. In some embodiments, a kit may contain instructions for topical application of the composition for treatment or protection of skin.

In another aspect, a method is provided for counteracting at least one effect of skin aging. The method may include administering a topical DPP and/or DPP extract containing formulation as described herein to an individual in need thereof by contacting a skin surface of the individual with the formulation. At least one effect of skin aging is ameliorated and/or visually improved as a result of contact of the pollen or extract thereof with the skin surface. In certain embodiments, amelioration and/or visual improvement of wrinkles, lines, skin dryness, dark spots, reduction in skin elasticity, increase in skin roughness, or a combination thereof is effected with the method. In one embodiment, the formulation may be administered topically to facial skin.

In another aspect, a method is provided for treating a skin condition. The method may include administering a topical DPP or DPP extract containing formulation as described herein to an individual in need thereof by contacting a skin surface of the individual with the formulation. At least one symptom of the skin condition is ameliorated, substantially eliminated, or eliminated as a result of contact of the pollen or extract thereof with the skin surface. In various embodiments, the skin condition may be selected from psoriasis, acne, atopic dermatitis, actinic keratosis, scleroderma, rosacea, eczema, an allergic skin disorder, radiation and/or chemotherapy induced mucositis, or a combination thereof. In some embodiments, the skin condition may include facial oil, enlarged facial pores, blackheads, or a combination thereof. In certain embodiments, the topical formulation may further contain one or more additional compound(s) for treatment of the skin condition, for example, a pharmaceutical compound for treatment of at least one symptom of the skin condition. The effects of the DPP or DPP extract and the additional compound(s) on at least one symptom of the skin condition may be additive or synergistic.

In another aspect, a method is provided for preventing a skin condition from developing, occurring, or worsening, or for lessening the severity of at least one symptom of a skin condition should it develop or occur. The method may include administering a topical DPP or DPP extract containing formulation as described herein to an individual in need thereof by contacting a skin surface of the individual with the formulation. At least one symptom of a skin condition is prevented or the severity lessened as a result of contact of the pollen or extract thereof with the skin surface. In one embodiment, the skin condition is skin cancer (e.g., melanoma), and administration of the topical formulation prevents skin cancer from developing or occurring or lessens the severity of at least one symptom of skin cancer should it develop or occur. In some embodiments, the skin condition is due to environmental skin damage, radiation therapy, chemotherapy, or photoaging. Environmental damage may include skin damage caused by sun exposure, and the topical formulation may be administered before, during, or after exposure of the skin surface to the sun. Environmental damage to skin may be caused, for example, by exposure to ultraviolet radiation (e.g., UVA and/or UVB radiation), infrared radiation, or a combination thereof. To prevent environmental damage caused by sun and/or ultraviolet and/or infrared radiation, the topical formulation may be formulated as a photoprotective composition, for example, a sunscreen.

In another aspect, a method is provided for delivery of one or more compound(s) to an external body surface, such as skin. The method may include administering a topical DPP or DPP extract formulation as described herein to an individual in need thereof by contacting an external body surface of the individual, such as a skin surface with the formulation. The compound(s) is (are) delivered to the skin as a result of contact of the formulation with the skin surface. In various embodiments, the compound may be selected from a steroidal compound, a plant steroidal compound, a glycoside compound, a gonadotrophic hormone, a carotenoid, a glucoprotein, a bioflavinoid, a triterpinoid, and an antioxidant, or a combination thereof. In some embodiments, the compound(s) to be delivered are contained within or derived from DPP or an extract thereof. In some embodiments, an estrogenic hormone (for example, estrone), a bioflavinoid (for example, rutin), and/or a triterpinoid (for example, β-amyrin), or a combination thereof, is delivered to an external body surface as a result of contact of a topical DPP or DPP extract containing composition as described herein with the body surface.

In another aspect, a method for preparing a topical formulation for treatment, amelioration, cure, prophylaxis, or prevention or lessening of severity of at least one symptom of a skin condition is provided. The method includes combining pollen from a palm species of the genus *Phoenix*, or an extract thereof, with at least one additional constituent to facilitate topical administration.

DETAILED DESCRIPTION

Formulations and methods for skin care, treatment of skin conditions, and anti-aging treatment are provided. The formulations and methods herein are based on the natural power stored in the reproductive cell of a palm of the genus *Phoenix*. This biological raw material may be harvested, processed and formulated in topical products. Topical application of the formulations described herein, for example, topical application of date palm pollen (DPP), may serve to delay the process of skin aging, and/or to counteract environmental factors that may damage the skin, and/or to treat and/or prevent a skin condition.

DEFINITIONS

Numeric ranges provided herein are inclusive of the numbers defining the range.

"A," "an" and "the" include plural references unless the context clearly dictates otherwise.

The terms "DPP," "date palm pollen," or "palm pollen," used interchangeably herein, refer to pollen from a species of the genus *Phoenix* in the family Palmae. The term "date palm" as used herein includes both ornamental and fruit-producing species in the genus *Phoenix*. As used herein, the term an "extract" of DPP refers to material that has been extracted from pollen from a species of the genus *Phoenix*.

The term "topical formulation" as used herein refers to a composition that is formulated for application to an external body surface, such as skin or mucous membranes.

The term "pharmaceutical" refers to a substance, e.g., a chemical substance, which may be used in medical treatment, cure, or prevention of a condition for which administration of the substance is beneficial, such as a disease condition.

The term "derived from" encompasses the terms "originated from," "obtained from," "obtainable from," "isolated from," and "created from," and generally indicates that one specified material finds its origin in another specified material or has features that can be described with reference to the another specified material.

The terms "recovered," "isolated," "purified," and "separated" as used herein refer to a material (e.g., a protein, nucleic acid, cell, or small molecule) that is removed from at least one component with which it is naturally associated. For example, these terms may refer to a material which is substantially or essentially free from one or more components which normally accompany it as found in its native state, such as, for example, an intact biological system.

"Unit dose" refers to an amount of a substance contained in a formulation for topical administration as described herein that is sufficient to cause a therapeutic, prophylactic, or cosmetic effect when applied to an external body surface of an individual. A unit dose may be administered in a single topical application of the formulation or in two or more applications.

A "compact disc" is a term that is well known in the pharmaceutical art and refers to a powder composition that has been formulated into a large tablet or compacted powder.

An "individual" refers to a mammal, often a human.

Date Palm Pollen

The formulations described herein include pollen from a palm in the genus *Phoenix* and/or an extract thereof. In some embodiments, pollen from a date palm is used. In one exemplary embodiment, the formulations herein include pollen from the species *Phoenix dactylifera* L, Palmae. The pollen can be harvested from male date palm trees during the flowering season in the months of February and March.

Pollen grains have been designed by nature to transfer genetic material from plant-to-plant. Date palm pollen (DPP) exists in a very fine powder material, produced by the male flowering date palm. The male flower develops 2-3 weeks before the female flower. Once the male pods open, they may be removed from the tree and dried. Once dried, pollen may be stored in a cool environment. DPP represents the reproductive cell of the male flower and contains the male contribution to the next generation of the plant.

Physico-Chemical Characteristics

DPP has unique size, shape and surface characteristics. Physico-chemical interaction of DPP with a biological surface may depend, for example, on particle size, micro-morphology, and/or surface geometry. Properties like flow, adhesion, and biochemical interactions with skin surface may be under the influence of any or all of these characteristics.

The size of DPP pollen grains is between 20 to 75 microns, for example, about 20, 25, 30, 35, 40, 45, 50, 55, 60, 65, 70, or 75 microns. In one embodiment, DPP has an average diameter of 50 microns. In other embodiments, DPP has an average diameter of about 24 microns. For example, in one embodiment, DPP is from the species *Phoenix dactylifera* L, Palmae and has a diameter of about 21 to about 27 microns, e.g., about 21, 22, 23, 24, 25, 26, or 27 microns, for example, a mean diameter of about 24 microns.

The shape is frequently elliptical. The surface is reticulate with irregular semi-circular pores and covered with spikes or needle like structures. The tip edges of the spikes are in the submicron range.

Dry DPP powder has excellent flow properties in addition to excellent spreading and adhesion properties on surfaces. DPP has both adhesive and spreading properties when applied to the skin. The flow properties of freshly-collected pollen depends on its moisture content; when dry, it is free flowing. The flow properties can be regulated by the addition of one or more flow regulating agent(s). Surface ruggedness of palm pollen permits it to adhere easily to biological surfaces. The spikes present on the surface allow the pollen to adhere to complex surface geometry and reach difficult-to-reach cracks on the skin surface.

In some embodiments, if the size of a single pollen grain is about 50 micron in average diameter, the amount of palm pollen grains required to cover the surface area of the average human face is about 100 mg. In some embodiments, if the size of a single pollen grain is about 24 microns in average diameter, the amount of palm pollen grains required to cover the surface area of the average human face is about 50 mg to about 100 mg. For example, in one embodiment, the size of a single pollen grain from the species *Phoenix dactylifera* L, Palmae is about 21 microns to about 27 microns, e.g., about 21, 22, 23, 24, 25, 26, or 27 microns, for example, a mean diameter of about 24 microns, and about 50 mg to about 100 mg of the palm pollen grains may be used to cover the surface area of the average human face.

Phytochemical Characteristics

Investigations have revealed that DPP contains estrone (Hassan and Abou el Wafa (1947) *Nature* 159(4038): 409). Estrone is an estrogenic hormone and is the predominant estrogen in postmenopausal women. DPP also contains rutin, a glycoside combination of the flavonol quercetin and the disaccharide rutinose that acts as an antioxidant. DPP also contains carotenoids, which are efficient free-radical scavengers, known to enhance the vertebrate immune system. A glucoprotein with gonadotrophic activity has been isolated from DPP. (Mahran et al. (1976) *Planta Med.* 29(2):171-175; El Ridi et al. (1952) *Arch Biochem Biophys* 39(2):317-21)

Topical Formulations

Compositions are provided that include palm pollen as described above, or an extract thereof, formulated for topical application to an external body surface. A composition herein may be formulated in any convenient form for topical administration. The form and components to be included in the composition will depend on the site of administration and intended use of the composition, as will be readily apparent to those of skill in the art. For example, the composition may be formulated as a powder, a compact disc, a suspension, a cream, a lotion, an ointment, a gel, a foam, a paste, an aerosol, a body wash, a hair product, a sunscreen, a lipstick, an emulsion, a cosmetic product, an anhydrous absorption base composition, or any composition that may be applied to an external body surface, for application of palm pollen or an extract thereof, and/or delivery of a substance, for example, a substance contained in palm pollen. In some embodiments, a composition is formulated for delivery of a unit dose of palm pollen, an extract thereof, or one or more compounds present in or derived from palm pollen, to an individual. A unit dose for application to a human face may contain, for example, about 50 to about 100 mg of date palm pollen, or an equivalent amount of date palm pollen extract. In some embodiments, the average diameter of a DPP grain is about 50 microns with an average density of about 0.6 g/cm$^3$ to about 0.8 g/cm$^3$. In other embodiments, the average diameter of a DPP grain is about 24 microns with an average density of about 0.8 g/cm$^3$ to about 0.9 g/cm$^3$. In some embodiments, the average diameter of a DPP grain from the species Phoenix dactylifera L, Palmae is about 24 microns with an average density of about 0.8 g/cm$^3$ to about 0.9 g/cm$^3$. In various embodiments, a unit dose, such as a unit dose for facial application, contains any of about 50, 55, 60, 65, 70, 75, 80, 85, 90, 95, or 100 mg of date palm pollen, or an equivalent amount of date palm pollen extract. For application to another external body surface, a unit dose may be determined by the ratio of the surface area of the body surface to the surface area of an average human face.

In some embodiments of the formulations described herein, an extract of date palm pollen is used. An extract may be prepared, for example, by extraction of one or more constituent(s), or all or substantially all constituents, of the pollen with one or more organic solvent(s). Extraction may be followed by evaporation, purification, and/or drying of the extract prior to incorporation into a formulation. A DPP extract contains one or more components of DPP and no or substantially no intact pollen grains. In some embodiments, a formulation as described herein may contain both DPP and an extract of DPP.

Typically, in addition to the palm pollen or extract thereof, a composition herein includes one or more additional constituents to facilitate topical application. In some embodiments, one or more flow regulating agent(s) is included. For example, silica (e.g., colloidal silica), silica gel, magnesium trisilicate, or cornstarch may be included as a flow regulating agent. A flow regulating agent may be included to increase flow of the formulation, depending on the application of use. A powder formulation or compact disc formulation may include one or more such flow regulating agent(s). A compact disc formulation may further include one or more filler(s), such as titanium dioxide, spray dried lactose, or starch, and may optionally further include one or more excipient(s) such as magnesium stearate to facilitate compression.

In some embodiments, the composition is formulated as a suspension, and in addition to palm pollen or an extract thereof, the suspension may contain one or more alcohol(s) Optionally, one or more preservative substance(s) may be included for storage and shelf life stability, such as, for example, benzalkonium chloride, benzyl alcohol, or parabens. Optionally, one or more suspending(s) agent may be included, for example, carboxymethyl cellulose or xanthan gum.

In some embodiments, the composition is formulated as a cream. In one embodiment, the cream is a vanishing cream formulation. A cream formulation may contain, in addition to palm pollen or an extract thereof, one or more surfactant(s), an oil phase, an aqueous phase, one or more preservative(s), and one or more stabilizer(s). A cream formulation may include one or more surfactants selected from, but not limited to, sorbitan monostearate, polysorbate 60, and polysorbate 20, one or more substance(s) forming and/or contained within the oil phase selected from, but not limited to, stearic acid, cetyl alcohol, isopropyl palmitate, isopropyl alcohol, glycerine, and polyethylene alcohol, a water-based aqueous phase containing substances in the formulation that are soluble in water and/or that segregate to the aqueous phase, one or more preservative(s) selected from, but not limited to, methylparaben, propylparaben, and benzyl alcohol, and one or more stabilizer(s) selected from, but not limited to, sorbitol, glycerine, and glyceryl laurate.

In some embodiments, the composition is formulated as a reconstituted milk suspension. A reconstituted milk suspension may contain dried palm pollen (for example, freeze dried or lyophilized palm pollen or an extract thereof) and a flow regulating agent, such as colloidal silica, which may be included as a dispersing agent. The dried pollen and flow regulating agent may be reconstituted in milk (e.g., homogenized and/or pasteurized milk).

In some embodiments, the composition is formulation as an anhydrous absorption base composition. For example, a liquid or semi-liquid anhydrous absorption base composition may contain, in addition to date palm pollen, one or more humectant(s) (one or more substance(s) that seals moisture in skin, e.g., act as moisturizers), for example, coconut oil, almond oil, lanolin; one or more surfactant(s) or emulsifier(s), for example, lecithin; and one or more consistency regulator(s) or thickener(s), for example, beeswax. For example, a cream (e.g., a thick cream) anhydrous absorption base composition may contain, in addition to date palm pollen, one or more humectant(s), for example, coconut oil, lanolin; one or more surfactant(s) or emulsifiers, for example, lecithin; and one or more consistency regulator(s) or thickener(s), for example, beeswax. For example, a solid anhydrous base composition may contain, in addition to date palm pollen, one or more humectant(s), for example, coconut oil; and one or more consistency regulator(s) or thickener(s), for example, beeswax.

Examples of compositions formulated as described above are provided in Tables 1 and 2. The formulations described in Tables 1 and 2 are exemplary and are not intended to be limiting. Other formulations may be prepared with other components and ratios of components by a person of skill in the formulation art and as adapted to have desired properties for a particular application of use. The formulation, manufacturing, and control of topical formulations such as creams, suspensions, sprays, etc. are known to pharmacists and others in the formulation art and are described in reference texts, such as Lachman L, Leiberman H, and Kanig J "The Theory and Practice of Industrial Pharmacy," published by Lea & Febiger (1986). Ratios of components in the formulations described herein may be adjusted by a person of skill in the formulation art based on optimum amounts necessary to provide maximum flow and stability.

In one embodiment, the composition contains DPP and one or more flow regulating agent(s) (e.g., colloidal silica) in a ratio to provide a powder formulation.

In another embodiment, the composition contains DPP, one or more filler(s) (e.g., titanium dioxide), and one or more flow regulating agent(s) (e.g., colloidal silica) in a ratio to provide a compact disc formulation.

In another embodiment, the composition contains DPP, one or more alcohol(s) (e.g., isopropyl alcohol), one or more preservative(s) (e.g., benzalkonium chloride), and water (e.g., demineralized water) in a ratio to provide a suspension. In some embodiments, the suspension is formulated as a sunscreen suspension or spray.

In another embodiment, the composition contains DPP, one or more surfactant(s) (e.g., sorbitan monostearate, polysorbate 60), one or more substance(s) forming and/or contained within an oil phase (e.g., stearic acid, cetyl alcoholisopropyl palmitate), and one or more substance(s) forming and/or contained within an aqueous phase (e.g., one or more preservative(s) (e.g., methylparaben, propylparaben);

one or more stabilizer(s) (e.g., sorbitol); water (e.g., distilled water)), in a ratio to provide a cream formulation (e.g., a vanishing cream formulation or a sunscreen cream or lotion).

In another embodiment, the composition contains DPP (e.g., freeze dried DPP), one or more flow regulating agent(s) (e.g., colloidal silica), and milk (e.g., homogenized pasteurized milk) in a ratio to provide a reconstituted milk suspension.

In another embodiment, the composition contains DPP, one or more humectant(s) (e.g., coconut oil, almond oil, and/or lanolin), one or more surfactant(s) (e.g., lecithin), and one or more thickener(s) (e.g., beeswax) in a ratio to provide a liquid or semi-liquid anhydrous absorption base formulation.

In another embodiment, the composition contains DPP, one or more humectant(s) (e.g., coconut oil and/or lanolin), one or more surfactant(s) (e.g., lecithin), and one or more thickener(s) (e.g., beeswax) in a ratio to provide a cream anhydrous absorption base formulation.

In another embodiment, the composition contains DPP, one or more humectant(s) (e.g., coconut oil), and one or more thickener(s) (e.g., beeswax) in a ratio to provide a solid anhydrous absorption base formulation.

TABLE 1

Exemplary DPP Formulations

| Formulation | Components | Amount | |
|---|---|---|---|
| DPP Powder formulation | Dry date palm pollen | 10 | g |
| | Colloidal silica | 0.01 | g |
| Compact discs | Dry date palm pollen | 10 | g |
| | Titanium dioxide | 0.1 | g |
| | Colloidal silica | 0.01 | g |
| DPP Suspension | Isopropyl alcohol | 50 | mL |
| | Dry date palm pollen | 10 | g |
| | Benzalkonium chloride | 0.01 | g |
| | Demineralized water | 100 | mL |
| DPP Vanishing cream | Stearic acid | 10 | g |
| | Cetyl alcohol | 1 | g |
| | Isopropyl palmitate | 1 | g |
| | Methylparaben | 0.1 | g |
| | Propylparaben | 0.05 | g |
| | Sorbitan monostearate | 2 | g |
| | Sorbitol 70% | 3 | g |
| | Polysorbate 60 | 1.5 | g |
| | Dry date palm pollen | 10 | g |
| | Distilled water to | 100 | g |
| Reconstituted DPP milk suspension | Freeze Dried date palm pollen | 1 | g |
| | Colloidal silica | 0.005 | g |
| | Reconstituted with homogenized pasteurized milk | to 10 | mL |
| Sunscreen Suspension or Spray | Isopropyl alcohol | 50 | mL |
| | Dry date palm pollen | 20 | g |
| | Benzalkonium chloride | 0.02 | g |
| | Demineralized water | 100 | mL |
| Sunscreen Cream or Lotion | Stearic acid | 10 | g |
| | Cetyl alcohol | 1 | g |
| | Isopropyl alcohol | 1 | g |
| | Methylparaben | 0.1 | g |
| | Propylparaben | 0.05 | g |
| | Sorbitan monostearate | 2 | g |
| | Sorbitol 70% | 3 | g |
| | Polysorbate 60 | 1.5 | g |
| | Dry date palm pollen | 15 | g |
| | Distilled water to | 100-125 | g |
| DPP Anhydrous Absorption Base (Liquid) | Coconut oil | 60 | g |
| | Almond oil | 15 | g |
| | Lanolin-anhydrous | 2 | g |
| | Lecithin | 1 | g |
| | Beeswax | 2 | g |
| | Dry date palm pollen | 20 | g |

TABLE 1-continued

Exemplary DPP Formulations

| Formulation | Components | Amount | |
|---|---|---|---|
| DPP Anhydrous Absorption Base (Semi-liquid) | Coconut oil | 45 | g |
| | Almond oil | 15 | g |
| | Lanolin - anhydrous | 2.5 | g |
| | Lecithin | 2.5 | g |
| | Beeswax | 15 | g |
| | Dry date palm pollen | 20 | g |
| DPP Anhydrous Absorption Base (Thick Cream) | Coconut oil | 57 | g |
| | Lanolin - anhydrous | 3.8 | g |
| | Lecithin | 3.8 | g |
| | Beeswax | 15.4 | g |
| | Dry date palm pollen | 20 | g |
| DPP Anhydrous Absorption Base (Solid) | Coconut oil | 39.7 | g |
| | Beeswax | 39.7 | g |
| | Dry date palm pollen | 20.6 | g |

TABLE 2

Exemplary DPP Formulations

| Formulation | Components | Amount |
|---|---|---|
| DPP Powder formulation | Dry date palm pollen | 99.5%-99.9%[1] |
| | Colloidal silica | 0.1%-0.5% |
| Compact discs | Dry date palm pollen | 90%-99.5% |
| | Colloidal silica | 0.01% to 1% |
| | Titanium dioxide | fill to 100% |
| DPP Suspension | Isopropyl alcohol | 50%-70% |
| | Dry date palm pollen | 10%-30% |
| | Benzalkonium chloride | 0.10%-5% |
| | Demineralized water | fill to 100% |
| DPP Vanishing cream | Stearic acid | 1%-10% |
| | Cetyl alcohol | 0.5%-1% |
| | Isopropyl palmitate | 0.5%-1% |
| | Methylparaben | 0.05%-0.1% |
| | Propylparaben | 0.01% to 0.05% |
| | Sorbitan monostearate | 1%-2% |
| | Sorbitol 70% | 3%-6% |
| | Polysorbate 60 | 1.5%-5% |
| | Dry date palm pollen | 10%-30% |
| | Distilled water | fill to 100% |
| Reconstituted DPP milk suspension | Freeze Dried date palm pollen | 10%-30% |
| | Colloidal silica | 0.05%-1% |
| | Reconstituted with homogenized pasteurized milk | fill to 100% |
| Sunscreen Suspension or Spray | Isopropyl alcohol | 30%-60% |
| | Dry date palm pollen | 10%-50% |
| | Benzalkonium chloride | 0.2%-0.5% |
| | Demineralized water | fill to 100% |
| Sunscreen Cream or Lotion | Stearic acid | 5%-10% |
| | Cetyl alcohol | 0.5%-1% |
| | Isopropyl alcohol | 0.5%-1% |
| | Methylparaben | 0.1% |
| | Propylparaben | 0.05% |
| | Sorbitan monostearate | 2%-3% |
| | Sorbitol 70% | 3%-5% |
| | Polysorbate 60 | 1.5%-3% |
| | Dry date palm pollen | 15%-30% |
| | Distilled water to | fill to 100% |
| DPP Anhydrous Absorption Base (Liquid/Semi-liquid) | Coconut oil | 45%-60% |
| | Almond oil | 10%-25% |
| | Lanolin - anhydrous | 1%-5% |
| | Lecithin | 1%-5% |
| | Beeswax | 2%-20% |
| | Dry date palm pollen | 10%-30% |
| DPP Anhydrous Absorption Base (Thick Cream) | Coconut oil | 45%-50% |
| | Lanolin - anhydrous | 2%-10% |
| | Lecithin | 2%-10% |
| | Beeswax | 20%-40% |
| | Dry date palm pollen | 10%-30% |

TABLE 2-continued

Exemplary DPP Formulations

| Formulation | Components | Amount |
|---|---|---|
| DPP Anhydrous Absorption Base (Solid) | Coconut oil Beeswax Dry date palm pollen | 30%-45% 30%-45% 10%-30% |

[1]% values in this table are expressed as weight percent (w/w).

Depending on the appropriateness for the application of use, any of the formulations herein may also include one or more fragrance(s).

A composition as described herein may be formulated for application to skin. In one embodiment, the composition is formulated for application to facial skin. In some embodiments, the composition is formulated for treatment, amelioration, cure, or prevention of a skin condition.

In some embodiments, the composition is formulated for use in a method to ameliorate at least one effect of aging. For example, the composition may be formulated for application to reduce one or more aging effects such as wrinkles, lines, skin dryness, dark spots, increase in skin roughness, or reduction in skin elasticity. In some embodiments, one or more effects of aging on facial skin is visibly reduced on facial skin by application of a topical formulation as described herein, and such effects may be substantially reduced or absent in visual appearance of facial skin that has received one or more applications of such a formulation.

In some embodiments, the composition is formulated for use in a method for treatment of a skin condition. In one embodiment, the skin condition may include facial oil (e.g., excessive facial oil), enlarged pores, blackheads, acne, or a combination thereof. Examples of other skin conditions that may benefit from application of topical formulations described herein include, but are not limited to, atopic dermatitis, actinic dermatosis, scleroderma, rosacea, eczema, allergic skin disorders. Examples of further skin conditions that may benefit from application of topical formulations described herein include, but are not limited to, radiation induced mucositis and chemotherapy induced mucositis. In certain embodiments, one or more additional substances may be included in the topical formulation for treatment of certain skin conditions. For example, one or more pharmaceutical(s) may be included. The additional substance(s), such as pharmaceutical(s), may have an effect on the skin condition that is additive or synergistic with the effect of palm pollen. In one embodiment, cortisone may be included in the formulation for treatment of an inflammatory skin condition.

In some embodiments, the composition is formulated for protection of skin, for example protection from environmental damage, and/or prevention of a skin condition. For example, the composition may be formulated as a photoprotective composition, to protect skin from harmful effects of sun exposure and/or prevention of skin cancer. In one embodiment, the composition is formulated as a sunscreen composition. A photoprotective composition herein may protect skin from ultraviolet radiation (e.g., UVA and/or UVB radiation) and/or infrared radiation. In another example, the composition may be formulated for protection of skin from radiation therapy and/or chemotherapy.

A composition as described herein may be formulated for delivery of one or more substance(s) to an exterior body surface of an individual. For example, the composition may be formulated for delivery of one or more substance(s) to the skin of an individual by topical application of a composition as described herein. In one embodiment, the composition is formulated for delivery of one or more substance(s) to the facial skin of an individual. The substance(s) to be delivered may be present in and/or derived from the palm pollen or extract thereof that is included in the composition. For example, a steroidal compound, a plant steroidal compound, a glycoside compound, a gonadotrophic hormone, a carotenoid, a glucoprotein, an antioxidant, a bioflavinoid, or a triterpinoid, or a combination of two or more of these substances, may be delivered in a composition as described herein. In one embodiment, the composition may be formulated for delivery an estrogenic compound, for example, estrone. In one embodiment, the composition may be formulated for delivery of a bioflavinoid, for example, rutin, and/or a triterpinoid, for example, β-amyrin. The composition may be formulated for delivery of one or more additional substance(s) that is not present in and/or derived from palm pollen, such as, for example, a pharmaceutical substance.

Methods of Use

A composition containing palm pollen or an extract thereof, as described above, may be topically applied to an external body surface of an individual in a method in which the composition provides a beneficial effect to the individual. For example, a composition as described above may be used in a method for treatment or prevention of a skin condition, for protection of skin from environmental damage, for visual improvement of the appearance of skin, or in a method to counteract an effect of aging. In the methods described herein, a composition described herein, for example, a composition as described in Table 1 or 2 (e.g., a powder, compact disc, suspension, cream, reconstituted milk suspension, anhydrous absorption base) may be applied topically. In other embodiments, a powder formulation may be sprinkled onto the skin from a container such as a perforated top container, for example, and applied with a soft brush. In another embodiment, a compact disc formulation may be applied using a brush, for example, a fine bristle brush. In another embodiment, a suspension formulation may be delivered to the skin via a pump, tube, bottle, spray, or similar delivery device and applied by hand. In a further embodiment, a cream or lotion may be supplied in a jar or tube (e.g., polyethylene tube), or spray device and applied by hand after delivery to the skin. In a still further embodiment, a reconstituted milk suspension may be reconstituted on site prior to application and applied, for example, by hand or as a scrub.

A formulation containing a unit dose of DPP may be applied topically once per day or more than once per day (e.g., 2, 3, or more times per day). A unit dose may contain, for example, about 50 mg to about 100 mg of DPP, or an extract from an equivalent amount of DPP. For example, a unit dose may contain about 50 mg, about 55 mg, about 60 mg, about 65 mg, about 70 mg, about 75 mg, about 80 mg, about 85 mg, about 90 mg, about 95 mg, or about 100 mg, or an extract from about 50 mg, about 55 mg, about 60 mg, about 65 mg, about 70 mg, about 75 mg, about 80 mg, about 85 mg, about 90 mg, about 95 mg, or about 100 mg of DPP.

A formulation as described herein may be applied topically, e.g., to a skin surface, for example, a facial skin surface, and either left on or removed after a period of time. In some embodiments, the formulation is applied topically to a skin surface, for example, a facial skin surface, and left on the skin surface. Other products that are designed to be applied and left on a skin surface, for example, but not limited to, moisturizer products, makeup foundation products, etc., may be applied over the topically applied formulation.

A method for counteracting at least one effect of aging is provided. A topical formulation containing palm pollen or an extract thereof is administered to a skin surface of an individual and at least one effect of skin aging is ameliorated, eliminated, or substantially eliminated from the treated skin as a result of such administration. For example, the composition may be administered to facial skin that contains one or more age-related skin conditions. One or more unit doses of palm pollen or an extract thereof may be administered as one or a series of administrations of the formulation with each administration containing a unit dose. In some embodiments, at least one effect of aging, such as wrinkles, lines, skin dryness, dark spots, reduction in skin elasticity, and/or increase in skin roughness is reduced is improved by such administration. In some embodiments, the treated skin visually has a more youthful appearance after topical treatment with a formulation as described herein, for example, improved visual surface appearance and/or reduction in visible pigment.

A method for treating a skin condition is provided. A topical formulation containing palm pollen or an extract thereof is administered to a skin surface of an individual and at least one symptom of a skin condition is ameliorated, eliminated, or substantially eliminated from the treated skin as a result of such administration. One or more unit doses of palm pollen or an extract thereof may be administered as one or a series of administrations of the formulation with each administration containing a unit dose. Nonlimiting examples of skin conditions that may be treated with the compositions described herein include psoriasis, acne, atopic dermatitis, actinic keratosis, scleroderma, rosacea, eczema, allergic skin disorders, radiation-induced mucositis, chemotherapy-induced mucositis, facial oil (e.g., excessive facial oil), enlarged pores, blackheads, or a combination thereof. In certain embodiments, the formulation may contain one or more additional compound(s) for treatment of the skin condition, such as a pharmaceutical compound. The effects of the palm pollen or extract thereof and an additional compound may be additive or synergistic. In some embodiments, a topical formulation containing palm pollen or an extract thereof as described herein is administered in conjunction with one or more additional, separate topical compositions, such as a composition that contains a pharmaceutical substance for treatment of the skin condition. Such separate composition(s) may have an effect that is additive or synergistic with the palm pollen or extract thereof. In some embodiments in the method for treating a skin condition, at least one symptom of a skin condition is reduced by at least about 5%, 10%, 20%, 30%, 40%, 50%, 60%, 70%, 80%, 90%, 95%, 98%, or 99%. In some embodiments, the skin condition is substantially eliminated or cured.

A method for preventing a skin condition from occurring or prophylactically lessening the severity of a skin condition is provided. A topical formulation containing palm pollen or an extract thereof is administered to a skin surface of an individual and at least one symptom of a skin condition is prevented, substantially prevented, or prophylactically lessened as a result of such administration. One or more unit doses of palm pollen or an extract thereof may be administered as one or a series of administrations of the formulation with each administration containing a unit dose. For example, environmental damage to skin or photoaging may be prevented, substantially prevented, or prophylactically lessened by application of the formulation before environmental exposure, for example, sun exposure. In one embodiment, skin cancer is prevented by use of the topical formulation prior to, during, or after sun exposure. The formulation may be in the form of a sunscreen or any formulation designed for photoprotection that is administered before, during, or after sun exposure. Use of the formulation may reduce, eliminate, or substantially eliminate environmental damage to skin caused by ultraviolet (e.g., UVA and/or UVB) and/or infrared radiation. In other examples, skin damage caused by radiation therapy and/or chemotherapy A method for delivery of at least one compound to an external body surface is provided. A topical formulation containing palm pollen or an extract thereof, as described herein, is administered to an external body surface of an individual, and at least one compound contained in the formulation is delivered to the body surface as a result of such administration. Nonlimiting examples of compounds that may be delivered in such a method include compounds present in or derived from palm pollen or an extract thereof, such as steroidal compounds, plant steroidal compounds, glycoside compounds, gonadotrophic hormones, carotenoids, glucoproteins, antioxidants, estrogenic hormones (e.g., estrone), bioflavinoids (e.g., rutin), and triterpenoids (e.g., β-amyrin). Added compounds that are not contained in or derived from the palm pollen or extract thereof, such as pharmaceutical compounds, may also be delivered to the body surface in a topical formulation as described herein.

Methods of Preparation

Methods for preparing any of the DPP and/or DPP extract containing compositions described herein are provided. The methods include combining pollen from a palm species of the genus *Phoenix*, or an extract thereof, with at least one additional constituent (component) to facilitate topical administration. In one embodiment, the method includes combining pollen or an extract thereof from *Phoenix dactylifera* L.

In one exemplary embodiment, preparation of the formulation includes the following steps: (1) mixing of non-DPP components, e.g., at a temperature less than about 50° C., or at a temperature lower than a temperature at which one or more protein(s) in DPP are denatured, or in circumstances in which an oleaginous phase is formed (for example, in an anhydrous formulation), the oleaginous phase may be melted at a temperature below about 60° C.; (2) addition of DPP or an extract thereof, e.g., at a temperature less than about 50° C., or at a temperature lower than a temperature at which one or more protein(s) in DPP are denatured; mixing and (3) mixing and homogenizing the formulation. It is desirable to avoid introduction of air, or to avoid introducing an amount of air that will oxidize and/or reduce activity of DPP, during the mixing and homogenization.

In one embodiment, the method includes combining DPP and one or more flow regulating agent(s) (e.g., colloidal silica) in a ratio to provide a powder formulation.

In another embodiment, the method includes combining DPP, one or more filler(s) (e.g., titanium dioxide), and one or more flow regulating agent(s) (e.g., colloidal silica) in a ratio to provide a compact disc formulation.

In another embodiment, the method includes combining DPP, one or more alcohol(s) (e.g., isopropyl alcohol), one or more preservative(s) (e.g., benzalkonium chloride), and water (e.g., demineralized water) in a ratio to provide a suspension. In some embodiments, the suspension is formulated as a sunscreen suspension or spray.

In another embodiment, the method includes combining DPP, one or more surfactant(s) (e.g., sorbitan monostearate, polysorbate 60), one or more substance(s) forming and/or contained within an oil phase (e.g., stearic acid, cetyl alcohol isopropyl palmitate), and one or more substance(s) forming and/or contained within an aqueous phase (e.g., one or more preservative(s) (e.g., methylparaben, propylparaben); one or more stabilizer(s) (e.g., sorbitol; water (e.g., distilled water)), in a ratio to provide a cream formulation (e.g., a vanishing cream formulation or a sunscreen cream or lotion).

In another embodiment, the method includes combining DPP (e.g., freeze dried DPP), one or more flow regulating agent(s) (e.g., colloidal silica), and reconstituting in milk (e.g., homogenized pasteurized milk) in a ratio to provide a reconstituted milk suspension.

In another embodiment, the method includes combining DPP, one or more humectant(s) (e.g., coconut oil, almond oil, and/or lanolin), one or more surfactant(s) (e.g., lecithin), and one or more thickener(s) (e.g., beeswax) in a ratio to provide a liquid or semi-liquid anhydrous absorption base formulation.

In another embodiment, the method includes combining DPP, one or more humectant(s) (e.g., coconut oil and/or lanolin), one or more surfactant(s) (e.g., lecithin), and one or more thickener(s) (e.g., beeswax) in a ratio to provide a cream anhydrous absorption base formulation.

In another embodiment, the method includes combining DPP, one or more humectant(s) (e.g., coconut oil), and one or more thickener(s) (e.g., beeswax) in a ratio to provide a solid anhydrous absorption base formulation.

Kits

Kits are provided for use in the methods described herein. The kits include a composition as described herein, for example including one or more unit dose of palm pollen or an extract thereof. Optionally, instructions for use and/or application, e.g., topical application, of the composition, are provided. Instructions may be provided in printed form or in the form of an electronic medium such as a CD or DVD, or in the form of a website address where such instructions may be obtained. Often, a unit dose of palm pollen or an extract thereof includes a dosage such that when administered to an individual, a therapeutically, prophylactically, or cosmetically effective level of palm pollen or an extract thereof is topically applied to an external body surface of the individual.

Suitable packaging is provided. As used herein, "packaging" refers to a solid matrix or material customarily used in a system and capable of holding within fixed limits a composition suitable for administration to an individual as described herein. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Kits may also optionally include equipment and/or dispensers for topical administration of a palm pollen formulation as described herein.

The following examples are intended to illustrate, but not limit, the invention.

EXAMPLES

Example 1

The raw material tested was fresh DPP, collected in the first week of March from male date palm trees (*Phoenix dactylifera* L). DPP was collected and air dried for 24 hours between 25 and 35° C. and stored in tight-sealed containers with dehydrating agents such as silica gel in the dark at −14 to −20° C.

DPP-containing formulations were administered to seven subjects ranging in age from 20 to 75. Powder, suspension, vanishing cream, and reconstituted milk formulations were prepared as described in Table 1. A small amount of DPP formulation (containing 0.1 gram pollen) was applied at nighttime and spread lightly to the face. This amount is sufficient to provide surface coverage for the average facial skin area. The formulations were also tested on the neck and arms of the subjects. The formulations were applied once daily for 5 to 7 days.

These formulations produced visible results from the first application. Skin revitalization and a smooth younger looking skin resulted after only a few applications.

After single topical application DPP acted as a gentle skin cleanser providing smooth skin regardless of age. After several applications there was a remarkable decrease in skin dryness, fine lines, and enlarged pores. An evident decrease in dark spots and facial oil was also observed. These remarkable results suggest that DPP may be an exciting natural alternative to other anti-aging products available to consumers.

Example 2

DPP from *Phoenix Dactylifera* L, Palmae grown in two different locations in Egypt was analyzed using optical and scanning electron microscope. Particle size, size distribution, shape and surface characteristics were determined using optical and scanning electron microscopy. No distinguishable differences in morphology were observed between the two samples.

The pollen grains examined were elliptical in shape with one deep furrow across the surface. The surface of the pollen is reticulate with irregular and semicircular pores. No distinguishable differences in pore frequency and surface roughness were observed between the two samples.

The particle size was between 21 and 27 microns, with a mean particle size of 24 microns. The particle size distribution obtained from image analysis is shown in Table 1.

TABLE 3

Particle size distribution using image analysis.

| Size Range (μm) | Average Particle Size (μm) | Percent distribution |
|---|---|---|
| 21-23 | 22 | 32 |
| 23-25 | 24 | 44 |
| 25-27 | 26 | 24 |

Example 3

DPP powder from *Phoenix Dactylifera* L, Palmae was tested for photoprotective properties for UV wavelengths between 290 and 400 nm. An SPF-2905 Analyzer System was used for FDA standard SPF testing and determination of other photoprotection parameters, using the standard protocol from the manufacturer, Optometrics. The protocol description from the manufacturer was as follows:

In-vitro analysis is performed using the SPF-2905 Analyzer and the latest version of WinSPF software. A 1-cc syringe is used to dispense 100 or more dabs of your sample over a Transpore® tape substrate area (70.7×70.7 mm) at the rate of 2 μl/cm$^2$, as specified by the U.S. Food and Drug Administration. Results are determined by averaging results of 18 scans of your sample in different locations on the Transpore® tape substrate. Each scan takes a transmittance measurement every 2 nm from 290 to 400 nm. These are compared to a reference scan at the same wavelength to compute the sample transmittance. The SPF-290S' WinSPF software converts measurements to the well-known SPF values, Boots Star ratings or Australian TNUV values using these established calculation methods."

SPF measures the UVB (290-320 nm) protection only. UVB rays represent about 5% of the total UV radiation reaching the earth. Other parameters that describe the photoprotective properties of DPP were also examined:
Critical UVA/UVB ratio
Boots Star rating
UVA/UV
Critical wavelength and area under UV absorption curve
For comparison, a commercially available sunscreen product labeled "SPF-30" was tested under the same conditions.
Results are summarized in Table 4.

TABLE 4

UV Absorption Parameters using Optometrics SPF-2905 Analyzer System

| | DPP | Commercial SPF-30 Product |
|---|---|---|
| SPF[1] | 7.14 | 10.83 |
| UVA/UVB Ratio[2] | 0.971 | 0.608 |
| Boots Star Rating (2004)[3] | 5 (Ultra) | 3 (Good) |
| UVA I/UV Ratio[4] | 0.95 (Highest) | 0.71 (High) |
| Max % T COV[5] | 694 | 364 |
| Critical Wavelength[6] | 386.5 | 374.3 |
| Curve Area[7] | 84.63 | 80.23 |

[1]SPF is defined as the ratio of the time required for a person's protected skin to redden after being exposed to sun-light compared to the time required for the same person's unprotected skin to redden.
[2]UVA/UVB Ratio indicates the ratio of UVA radiation protection to the UVB protection.
[3]Boots Star Rating is an in vitro method used to describe the ratio of UVA to UVB protection offered by sunscreen,, with 5 as the highest value on this scale.
[4]UVA I/UV Ratio indicates ratio of UVAI (340-400 nm range) absorbance to total UV absorbance.
[5]Max % T COV is defined as % maximum transmission coverage.
[6]Critical wavelength represents the wavelength below which 90% of the total area under the UV absorption curve falls. The American Academy of Dermatology recently endorsed a critical wavelength of 370 nm as a measure of effective UVA protection, and recommended that the FDA use this as a requirement for those sunscreens labeled as "broad spectrum" coverage. A higher critical wavelength indicates better UV protection, particularly at higher wavelength UVA radiation.
[7]Curve area indicates the area under the absorption/ultraviolet wavelength curve. Higher surface area under the curve indicates greater UV protection.

Example 4

The effectiveness of DPP in treatment of the effects of photoaging was investigated using Visia™ Complexion Analysis. This method is based on digital image analysis and was used to quantitatively evaluate the effectiveness of daily application of DPP from *Phoenix Dactylifera* L, Palmae in visible reversal of the effects of photoaging over a 35-day period.

Visia™ uses high resolution facial photographs to test for 6 characteristics of skin (texture, spots, UV spots, wrinkles, pores and porphyrins). It measures feature counts (the number of times a feature is seen. For example, for pores, it will count the number of pores on a predetermined area on the face. It also measures absolute values. For example, in the case of pores, it will measure the pores in proportion to the predetermined area.

Photoaging is the premature aging of the skin due to chronic exposure of skin to ultraviolet (UV) light, for example, from the sun or tanning beds. Photoaging manifestations may include wrinkles and discolored skin spots, and may further include actinic keratosis and pre-cancerous lesions.

This study was carried out on 3 subjects (1 male, 2 female, 37-60 years) who were instructed to apply 20% DPP suspension every evening for 35 days. The suspension used in this study contained 20% DPP (w/w) and 80% isopropyl alcohol (w/w). Each subject received a 2 oz dropper bottle and was asked to apply 5 drops to each side of the face (after washing) every evening.

Quantitative measurements of wrinkles, texture, spots, UV spots, pores and porphyrins were made at baseline, 15 and 35-day time-points. Results are reported below (Tables 5 and 6) both in the feature counts and absolute scores.

Feature counts offer a count of the number of discrete instances of the feature being evaluated, without regard to the size or intensity of each instance. Feature count is the number of the characteristic (not the area). This was calculated for each subject based on baseline value. The difference between the first and second value represents the absolute change. This value was converted to a percentage. (Value−baseline divided by baseline×100). Negative values indicate a decrease in the feature count, and positive values indicate an increase in feature count.

Absolute scores provide comprehensive measurement of the impact that the feature has on complexion, factoring in the total size and area as well as intensity of detected instances of the feature being analyzed. Absolute score represents surface area of the characteristic and represents a measure of the impact of usage of DPP. This was calculated for each subject based on baseline value. The difference between the first and second value represents the absolute change. This value was converted to a percentage. (Value−baseline divided by baseline×100). Negative values indicate a decrease in the absolute score, and positive values indicate an increase in absolute score.

TABLE 5

Visia ™ Complexion Analysis percent change in number (Feature Count)

| | % Change after 15 days | | | | % Change after 35 days | | | |
|---|---|---|---|---|---|---|---|---|
| Feature | Subject A | Subject B | Subject C | Mean | Subject A | Subject B | Subject C | Mean |
| Spots | +2.8 | −6.2 | −12.8 | −5.4 | +2.8 | −21.5 | −11.3 | −10 |
| Wrinkles | −25 | +8.0 | +6.7 | −3.4 | N/A | −32 | +60 | +14 |
| Texture | −15.7 | −20.9 | −3.6 | −13.4 | +21 | −38.9 | −33.8 | −17.2 |
| Pores | −13.6 | −7.9 | +4.1 | −5.8 | +3.7 | −29.4 | −13.9 | −13.2 |
| Porphyrins | −58.9 | +9.0 | N/A | −24.5 | −59 | −30.3 | N/A | −44.7 |
| UV spots | +73.6 | 0 | −5.6 | +22.7 | +69.6 | +8.5 | −9.0 | +23.0 |

[1]"N/A" in Tables 5 and 6 indicates that no value was recorded.

TABLE 6

Visia ™ Complexion Analysis percent change in Absolute Scores (Impact)

| Feature | % Change after 15 days | | | | % Change after 35 days | | | |
|---|---|---|---|---|---|---|---|---|
| | Subject A | Subject B | Subject C | Mean | Subject A | Subject B | Subject C | Mean |
| Spots | −2.6 | −7.9 | −19.8 | −10.1 | −2.5 | −4.6 | −13.4 | −6.8 |
| Wrinkles | −45.3 | +13 | +22.8 | −3.2 | N/A | −37.9 | +17.5 | −10.2 |
| Texture | −19.1 | −18.9 | +1.6 | −12.1 | +20.5 | −30.7 | −30.3 | −13.5 |
| Pores | −15.4 | −12.4 | +6.3 | −7.16 | −2.1 | −13 | −13.3 | −9.5 |
| Porphyrins | −56 | +11.2 | N/A | −22.4 | −63.5 | −8.7 | N/A | −36.1 |
| UV spots | +94.2 | 0 | +5.4 | +33.2 | +64 | +35.5 | +9.3 | +36.3 |

A dramatic decrease in the number and size of spots and pores was observed in all test subjects. The porphyrins (bacterial excretion that can be lodged in the pores) decreased and the texture (skin roughness) improved.

There was a significant increase in ultraviolet spots detected by UV photography. Although not wishing to be bound by theory, this could indicate an increase in melanin production, which could be beneficial in melanoma prevention.

The outer surface of DPP may provide a microbrush-like function that massages the skin and cleans difficult to reach debris, foreign bodies and dead cells at the surface of the skin. This mechanical action may provide a resurfacing of the outer layer of the epidermis. Although not wishing to be bound by theory, this physical and mechanical action may explain the decrease in porphyrins, pores (number and size), and surface roughness.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention, which is delineated in the appended claims.

All publications, patents, and patent applications cited herein are hereby incorporated by reference in their entireties for all purposes and to the same extent as if each individual publication, patent, or patent application were specifically and individually indicated to be so incorporated by reference.

We claim:

1. A composition formulated for topical application, comprising pollen from a palm species of the genus *Phoenix*, or an extract thereof, in admixture with at least one additional constituent to facilitate topical application of the composition, wherein the at least one additional constituent comprises about 45% w/w to about 60% w/w coconut oil and about 2% w/w to about 10% w/w lanolin, and/or comprises about 20% w/w to about 40% w/w beeswax.

2. The composition according to claim 1, wherein the pollen or extract thereof is from *Phoenix dactylifera* L.

3. The composition according to claim 1, wherein said composition is formulated as a suspension, a cream, a lotion, an ointment, a gel, a foam, a paste, an aerosol, a body wash, a hair product, a sunscreen, a lipstick, an emulsion, a cosmetic, or an anhydrous absorption base composition.

4. The composition according to claim 3, further comprising a fragrance.

5. A composition according to claim 1, formulated as a cream or a lipstick.

6. A kit comprising the composition according to claim 1.

7. The kit according to claim 6, further comprising instructions for topical application of the composition for treatment or protection of skin.

8. A method for preparing the topical composition according to claim 1, comprising combining pollen from a palm species of the genus *Phoenix*, or an extract thereof, with at least one additional constituent to facilitate topical administration of the composition, wherein the at least one additional constituent comprises about 45% w/w to about 60% w/w coconut oil and about 2% w/w to about 10% w/w lanolin, and/or comprises about 20% w/w to about 40% w/w beeswax.

9. The method according to claim 8, wherein the pollen or extract thereof is from *Phoenix dactylifera* L.

10. The method according to claim 8, wherein the topical composition is formulated as a cream or lipstick.

11. A method for counteracting at least one effect of skin aging, comprising administering an effective amount of the topical composition according to claim 1 to an individual in need thereof, wherein the method comprises contacting a skin surface of the individual with the composition, and wherein at least one effect of skin aging is ameliorated by contact of the composition with the skin surface.

12. The method according to claim 11, wherein the at least one effect of skin aging comprises wrinkles, lines, skin dryness, dark spots, reduction in skin elasticity, increase in skin roughness, or a combination thereof.

13. A method of treating a skin condition, comprising administering an effective amount of the topical composition according to claim 1 to an individual in need thereof, wherein the method comprises contacting a skin surface of the individual with the composition, and wherein at least one symptom of the skin condition is ameliorated by contact of the composition with the skin surface.

14. The method according to claim 13, wherein the skin condition is selected from psoriasis, acne, atopic dermatitis, actinic keratosis, scleroderma, rosacea, eczema, an allergic skin disorder, radiation-induced mucositis, and chemotherapy-induced mucositis.

15. A method of preventing or lessening the severity of a skin condition, comprising administering an effective amount of the topical composition according to claim 1 to an individual in need thereof, wherein the method comprises contacting a skin surface of the individual with the composition, and wherein at least one symptom of a skin condition is prevented or the severity lessened by contact of the composition with the skin surface.

16. The method according to claim 15, wherein the skin condition comprises environmental skin damage, skin damage associated with radiation therapy, skin damage associated with chemotherapy, or photoaging.

17. The method according to claim 16, wherein the environmental damage comprises skin damage caused by sun exposure and the topical composition is administered before or after exposure of the skin surface to the sun.

* * * * *